(12) United States Patent
Nagasaki et al.

(10) Patent No.: US 9,333,265 B2
(45) Date of Patent: May 10, 2016

(54) ORGANIC-INORGANIC HYBRID COMPOSITE OF POLYMERIZED NITROXIDE COMPOUND AND INORGANIC PARTICLES

(71) Applicants: UNIVERSITY OF TSUKUBA, Ibaraki (JP); TSUKUBA UNIVERSITY OF TECHNOLOGY, Ibaraki (JP)

(72) Inventors: Yukio Nagasaki, Ibaraki (JP); Yutaka Ikeda, Ibaraki (JP); Toru Yoshitomi, Ibaraki (JP); Tatsuya Yaguchi, Ibaraki (JP); Mayo Yamashita, Ibaraki (JP); Md. Amran Hossain, Ibaraki (JP); Tomoki Yoshinari, Ibaraki (JP); Atsushi Ueda, Ibaraki (JP); Aki Hirayama, Ibaraki (JP)

(73) Assignees: UNIVERSITY OF TSUKUBA, Ibaraki (JP); TSUKUBA UNIVERSITY OF TECHNOLOGY, Ibaraki (JP)

(*) Notice: Subject to any disclaimer, the term of this patent is extended or adjusted under 35 U.S.C. 154(b) by 0 days.

(21) Appl. No.: 14/376,985

(22) PCT Filed: Feb. 6, 2013

(86) PCT No.: PCT/JP2013/052769
§ 371 (c)(1),
(2) Date: Nov. 25, 2014

(87) PCT Pub. No.: WO2013/118783
PCT Pub. Date: Aug. 15, 2013

(65) Prior Publication Data
US 2015/0118310 A1    Apr. 30, 2015

(30) Foreign Application Priority Data
Feb. 7, 2012  (JP) .................... 2012-024460

(51) Int. Cl.
*C08L 25/18* (2006.01)
*C08L 71/00* (2006.01)
(Continued)

(52) U.S. Cl.
CPC .............. *A61K 47/34* (2013.01); *A61K 9/0009* (2013.01); *A61K 9/5115* (2013.01);
(Continued)

(58) Field of Classification Search
CPC . A61K 47/02; A61K 47/34; A61K 47/48861; A61K 9/0009; A61K 9/5115; A61K 9/5146; A61K 2300/00; A61K 31/77; A61K 31/787; C01B 33/18; C08G 85/00; C08K 3/10; C08K 3/36; C08K 2003/0856; C08K 2003/2265; C08L 53/00; C08L 101/025; C08L 101/06; C08L 25/18; C08L 71/00
See application file for complete search history.

(56) References Cited

U.S. PATENT DOCUMENTS 6,001,905 A    12/1999  Steinmann
6,541,039 B1 *  4/2003  Lesniak ............. A61K 41/0052
                                                 424/422

(Continued)

FOREIGN PATENT DOCUMENTS

JP    10-298280     11/1998
JP    2008-525600    7/2008
(Continued)

OTHER PUBLICATIONS

International Search Report issued Apr. 23, 2013 in International (PCT) Application No. PCT/JP2013/052769.
(Continued)

*Primary Examiner* — Aradhana Sasan
(74) *Attorney, Agent, or Firm* — Wenderoth, Lind & Ponack, L.L.P.

(57) ABSTRACT

Provided is an organic-inorganic hybrid composite of a polymerized cyclic nitroxide radical compound and inorganic nanoparticles. Such a composite is capable, for example, of maintaining a stable nanoparticle shape in gastric fluid, and can be used by itself or as a carrier for delivery of another drug to the intestines.

15 Claims, 6 Drawing Sheets

(51) Int. Cl.
*C08L 101/02* (2006.01)
*C08L 101/06* (2006.01)
*C08L 53/00* (2006.01)
*C01B 33/18* (2006.01)
*A61K 47/34* (2006.01)
*C08K 3/10* (2006.01)
*C08K 3/36* (2006.01)
*A61K 9/00* (2006.01)
*A61K 9/51* (2006.01)
*A61K 31/77* (2006.01)
*C08G 85/00* (2006.01)
*A61K 47/48* (2006.01)
*A61K 47/02* (2006.01)
*A61K 31/787* (2006.01)

(52) U.S. Cl.
CPC .............. *A61K 9/5146* (2013.01); *A61K 31/77* (2013.01); *A61K 31/787* (2013.01); *A61K 47/02* (2013.01); *A61K 47/48861* (2013.01); *C01B 33/18* (2013.01); *C08G 85/00* (2013.01); *C08K 3/10* (2013.01); *C08K 3/36* (2013.01); *C08L 25/18* (2013.01); *C08L 53/00* (2013.01); *C08L 71/00* (2013.01); *C08L 101/025* (2013.01); *C08L 101/06* (2013.01)

(56) References Cited

U.S. PATENT DOCUMENTS

| | | | |
|---|---|---|---|
| 8,703,083 B2* | 4/2014 | Solovyov | B01D 53/565 131/331 |
| 2003/0143215 A1* | 7/2003 | Miyata | A61K 38/51 424/94.4 |
| 2006/0142541 A1 | 6/2006 | Hossainy | |
| 2008/0206306 A1 | 8/2008 | Hossainy | |
| 2008/0293893 A1 | 11/2008 | Hossainy | |
| 2008/0311397 A1* | 12/2008 | Tatsumi | C01B 37/02 428/402 |
| 2011/0142787 A1 | 6/2011 | Nagasaki et al. | |
| 2014/0356315 A1 | 12/2014 | Nagasaki et al. | |

FOREIGN PATENT DOCUMENTS

| | | |
|---|---|---|
| JP | 2011-173960 | 9/2011 |
| JP | 2011-184429 | 9/2011 |
| JP | 2012-111700 | 6/2012 |
| WO | 2009/133647 | 11/2009 |
| WO | 2013/111801 | 8/2013 |

OTHER PUBLICATIONS

Extended European Search Report issued Aug. 13, 2015, in corresponding European Application No. 13746757.7.

* cited by examiner

ORGANIC-INORGANIC HYBRID COMPOSITE OF POLYMERIZED NITROXIDE COMPOUND AND INORGANIC PARTICLES

TECHNICAL FIELD

The present invention relates to an organic-inorganic composite of a polymerized cyclic nitroxide radical compound and silica or magnetic particles, and to a use therefor.

BACKGROUND ART

In recent years, it has become clear that excess reactive oxygen species (ROS) are produced in living bodies due to irregular lifestyles, aging, social stress and the like, leading to a variety of chronic conditions (arteriosclerosis, diabetes, etc.) and intractable diseases (Alzheimer's, Parkinson's, etc.). Normally the oxidation-antioxidation (redox) balance is strictly regulated in vivo, but when excess ROS are produced, the balance of oxidation-antioxidation factors shifts towards oxidation. Various antioxidants have been studied in the past for preventing chronic conditions, but in the case of low-molecular-weight antioxidants, the effective dose is low because they inhibit mitochondrial electron transport and other essential reactions in the body when administered at high doses and for reasons of kidney excretion and metabolism, and these antioxidants are also problematic because they disperse through the body, causing systemic side-effects. Attempts have also been made to treat and prevent oxidative stress disease with low-molecular-weight antioxidants, but the effects have not been impressive.

Therefore, the inventors have developed a novel nano-therapy for eliminating ROS in necessary areas, using a self-assembling nanoparticle (nitroxide radical-containing nanoparticle: RNP) comprising a nitroxide radical as a catalytically functioning ROS scavenger, enclosed in a polymer chain (Patent Document 1).

Subsequently, the inventors have confirmed and disclosed in a still-unpublished patent application description that such an RNP is retained long-term in the blood vessels in the form of a nanoparticle after intravenous administration, and has a strong therapeutic effect against cerebral infarction, myocardial infarction and acute renal failure when it breaks down in tissue subject to oxidative stress.

Considering these circumstances, the inventors have developed a novel therapy for eliminating ROS in necessary areas, using a self-assembling nanoparticle enclosing a nitroxide radical as a catalytically functioning ROS scavenger (Patent Document 1). They have also provided a composition comprising such an RNP together with another drug such as a low-molecular-weight antioxidant (Patent Document 2). This document describes the use of the composition as a medicinal preparation for oral administration, but does not describe the effects of actual oral administration. Moreover, the inventors have confirmed that a cationically chargeable RNP itself or a conjugate (forming a polymer micelle in an aqueous medium) of an anionic drug encapsulated in the RNP using the property of cationic chargeability is retained long-term in the blood vessels in the form of a nanoparticle after intravenous administration, and is therapeutically effective against cerebral infarction, myocardial infarction and acute renal failure caused by oxidative stress because the micelle or particle breaks down in tissue subject to oxidative stress (see Patent Document 1 in part, and currently unpublished patent application in part).

However, in some cases the modes of use of this RNP are limited by its property of breaking down in tissue subject to oxidative stress, and by the subsequently discovered property of rapidly breaking down in acidic environments such as gastric fluid.

CITATION LIST

Patent Literature

Patent Document 1: WO 2009/133647
Patent Document 2: JP 2011-184429 A

SUMMARY OF THE INVENTION

Problems to be Solved by the Invention

It is an object of the invention to provide a material or composite, or a drug-encapsulating conjugate or composite of RNP that can be used stably under various physiological conditions including acidic environments and that, if possible, incorporates new properties while retaining the characteristics of RNP.

Means of Solving the Problems

If such a material or composite could be provided, it would be possible to construct a drug delivery system whereby a drug could exist stably in an RNP in the acidic environment of the stomach for example, and be delivered efficiently to the intestines without being digested.

Although this is not a limitation, it is also possible that the function of a peritoneal dialysate could be improved for example if the new property of removing waste material present in body fluid and the like could be provided in addition to the properties described above. Peritoneal dialysis is a treatment method that has been developed to treat kidney failure patients whose kidney functions are depressed due to the effects of various diseases in recent years in the context of an aging society. This method is used together with hemodialysis, in which blood is purified by extracorporeal circulation using a dialyzer. Although it allows easier rehabilitation and is superior from the standpoint of protecting remaining renal function, peritoneal dialysis is still used less than hemodialysis because it has not been possible to resolve problems of complex dialysate replacement and peritoneal sclerosis. It has pointed out that one cause of peritoneal sclerosis is the oxidative stress caused by excess reactive oxygen species produced especially at high sugar concentrations. Thus, it is thought that the usage rate of peritoneal dialysis, with all its advantages, could be increased if a system could be provided whereby the superior an antioxidative effects of RNPs could be maintained while suppressing oxidative stress occurring during peritoneal dialysis and providing the function of adsorbing waste products in order to improve peritoneal dialysis efficiency. Moreover, an RNP effectively encapsulating magnetic nanoparticles could be used for example in magnetic hyperthermia due to the effect of the magnetic nanoparticles, without adversely affecting the antioxidative function of the polymerized cyclic nitroxide radical compound that is another constituent element of the RNP, and could also serve as a base for cell separation and isolation (screening) of specific biological molecules.

From such a perspective, it was discovered as a result of research aimed at improving the functions of RNPs that silica or magnetic particles could be efficiently encapsulated in an RNP or polymer micelle, or else silica or magnetic particles could be coated with a polymerized cyclic nitroxide radical compound. Moreover, an RNP or polymer micelle encapsulating such inorganic particles maintains a stable micelle shape or particle shape in physiological environments better than one containing no inorganic particles, and even in an acidic environment of pH 3 in the case of a specific RNP for example. It was also discovered that a particle comprising a drug contained in such an RNP is also stable in physiological environments. Moreover, it was also confirmed that, when administered to the peritoneal membrane of a peritoneal inflammation model rat, an RNP encapsulating silica strongly suppresses deterioration of the peritoneal membrane.

Thus, an organic-inorganic composite is provided here, in which the organic component is a block copolymer represented by General Formula (I) below, and the inorganic component is an inorganic particle selected from the group consisting of silica and magnetic nanoparticles.

$$\text{PEG-CNR} \quad (I)$$

In the formula, PEG is a segment containing polyethylene glycol), and CNR is a polymer segment having a repeating unit containing, as part of a pendant group, a cyclic nitroxide radical that binds to the polymer main chain via a linking group, preferably a linking group having at least one imino (—NH—) or oxy (—O—).

As one embodiment of an organic-inorganic composite containing an inorganic particle and the block copolymer represented by General Formula (I) above, a composite in the form of particles having an average particle diameter of 3 nm to 1 mm or preferably 5 nm to 500 nm or still more preferably 5 nm to 100 nm or yet more preferably 10 nm to 50 nm when dissolved or dispersed in water is generally desirable. Although not limited, such a composite is suited to in vivo use when the particles are nanometers in size (so-called nanoparticles), but in particular when the inorganic particles are magnetic particles and are used in so-called bioseparation (separation or isolation of biological molecules or cells), the composite of the present invention may be in the form of particles having an average particle diameter of 500 nm to 1 mm or preferably 1 μm to 500 μm or more preferably 1 μm to 100 μm or still more preferably 1 μm to 50 μm, rather than nanoparticles.

As another embodiment of the invention, a peritoneal dialysate is provided containing as active ingredients at least the composite described above and a pharmacologically acceptable diluent or carrier.

The aforementioned composite further containing an anionic drug is provided as yet another embodiment of the invention.

With an RNP formed from this organic-inorganic composite, the inorganic particles can be dispersed and retained uniformly in bodily fluid because the particles are encapsulated in the RNP, the particle shape of the RNP can be maintained in bodily fluid due to the effect of the encapsulated inorganic particles, and can be retained for a certain period of time even in acidic bodily fluid in particular when the block copolymer represented by General Formula (I) above includes at least one imino group as a linking group and the inorganic particles are silica, and another drug can also be encapsulated stably in the RNP at a high concentration.

DETAILED DISCLOSURE OF THE INVENTION

The size and shape of the inorganic particles may be changed according to the intended use of the organic-inorganic particles to be provided, but particles in the range of a few nm to a few mm in average diameter are intended. When such particles are silica particles, those sold commercially as Methanol Silica Sol, MEK-ST or Snowtex O (supplied by Nissan Chemical Industries, Ltd.) may be included in the composite, either as is or after purification. The shape of such inorganic particles is not limited, but may be spherical, cubic, cuboid or 8- to 16-sided or the like. The particle diameter of such particles is represented as the corresponding value of a spherical particle.

Although the magnetic nanoparticles are also not limited, it is desirable to use those that are used or proposed for use in the technical field as biomedical magnetic nanoparticles or for bioseparation, or for example magnetite ($Fe_3O_4$) or magnehemite ($\gamma$-$Fe_2O_3$) or intermediates of these (supplies by JSR Life Sciences Corporation). Moreover, the magnetic nanoparticles may specifically be FePt nanoparticles (in which the average content ratio of Fe is 35 atoms or more) (see for example JP 2009-57609 A). In the present invention, magnetic nanoparticles that have been surface modified with carboxyl groups or sulfone groups are sometimes advantageous for maintaining the stability of the particles in the composite. Thus, the composite may contain one or more kinds of magnetic particles selected from the group consisting of $Fe_3O_4$, $\gamma$-$Fe_2O_3$ and FePt.

In the block copolymer represented by General Formula (I) above, the cyclic nitroxide radical is bound to the polymer main chain via a linking group represented by o- or p-phenylene-$C_{1-6}$ alkylene—NH—($C_{1-6}$ alkylene)$_q$- or o- or p-phenylene-$C_{1-6}$ alkylene—O—($C_{1-6}$ alkylene)$_q$- (in which q is an integer from 0 to 1 or preferably 0), and the cyclic nitroxide radical is selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl.

The polymer main chain here is derived from polymerizable unsaturated double bonds, and unbound termini of the phenylenes bind to this main chain. The descriptions of Patent Document 1 may be consulted with respect to the structure of such a polymer main chain (Patent Document 1 is incorporated by reference into the content of this Description).

A more specific instance of the block copolymer represented by General Formula (I) is given by General Formula (II).

[Chemical formula 1]

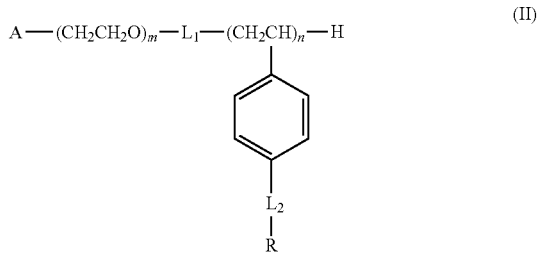

In the formula, A represents an unsubstituted or substituted $C_1$-$C_{12}$ alkoxy, with the substituent if any being a formyl group or a group represented by $R^1R^2CH$— (in which $R^1$ and $R^2$ are independently $C_1$-C4 alkoxy groups or $R^1$ and $R^2$ together form —$OCH_2CH_2O$—, —$O(CH_2)_3O$— or —$O(CH_2)_4O$—); $L_1$ is selected from the group consisting of a single bond, —$(CH_2)_cS$— and —$CO(CH_2)_cS$— (in which c is an integer from 1 to 5); $L_2$ is —$C_{1-6}$ alkylene—NH—($C_{1-6}$ alkylene)$_q$— or —C$_{1-6}$ alkylene—O—(C$_{1-6}$ alkylene)$_q$— (in which q is 0 or 1); R represents a residue of a cyclic nitroxide radical compound selected from the group consisting of 2,2, 6,6-tetramethylpiperidine-1- oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxazolidine-3-oxyl-2-yl, 2,4, 4-trimethyl-1,3-thiazolidine-3-oxyl-2-yl and 2,4,4-trimethyl-imidazolidine-3-oxyl-2-yl, L$_2$-R may be present in 50% or preferably 70% or more preferably 80% or more preferably 95% of the total number n, and when it is not present, the remaining L$_2$-R parts may be methyl, halo (such as chloro, brome or iodo)methyl or hydroxymethyl groups; m is an integer from 20 to 5,000, or preferably 20 to 1,000, or more preferably 20 to 500; n is independently an integer from 3 to 1,000, or preferably 3 to 500, or more preferably 3 to 100, or especially 5 to 50; and more preferred examples of R are the groups represented by the following formulae:

[Chemical formula 2]

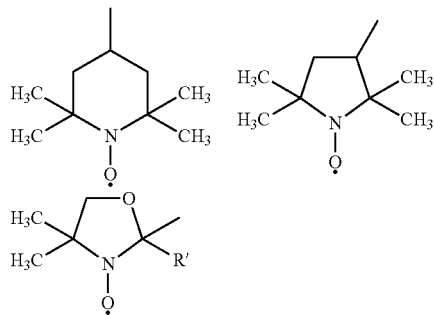

in which R' is a methyl group.

The block copolymer above is either described in Patent Document 1, or may be manufactured by the described methods.

The organic-inorganic hybrid composite may be produced by simply mixing the inorganic particles and the aforementioned block copolymer in a powdered state at between room temperature and 90° C. In general, this composite can be produced by dissolving or dispersing and mixing the two either buffered or unbuffered in an aqueous medium containing an aqueous organic solvent such as dimethyl formamide (DMF), dimethyl sulfoxide (DMSO), dimethylacetamide, methanol, ethanol or the like as necessary. Such a composite can be provided as particles or polymer micelles formed via a self-assembly process during preparation. It can also be provided as a dried or preferably freeze-dried product of the particles or polymer micelles thus formed. The particle diameter of the particles depends on the size of the inorganic particles used as a starting material, and in general the inorganic particles of the starting material can have an average diameter in the range of a few nm to a few mm, or specifically 3 nm to 1 mm, or generally 3 nm to 500 µm, or preferably 5 nm to 100 nm, or more preferably 5 nm to 80 nm, or especially 10 nm to 50 nm. When the particles are magnetic particles, particles with an average particle diameter of 500 nm to 10 mm or preferably 1 µm to 500 nm or more preferably 1 µm to 100 µm or still more preferably 1 µm to 50 µm can be used. As used here, particle diameter means a value that can be confirmed by dynamic light scattering (DLS) measurement of composite particles dissolved or dispersed in an aqueous medium.

The content ratio of the inorganic particles and the block copolymer in the composite is not limited as long as the composite particles can be observed as having the aforementioned particle diameter in an aqueous medium. Thus, a person skilled in the art can select appropriate content ratios and try forming composite particles in accordance with the composite particle manufacturing methods describe below, and measure them by dynamic light scattering to select a suitable content ratio in the present invention. However, although this is not a limitation, in the case of a block copolymer represented by General Formula (II) above in which the m of the poly(ethylene glycol) segment is 20 to 5,000 and n is 3 to 1,000, if the inorganic particles are silica particles with an average diameter of 30 nm to 50 nm, the weight ratio (polymer:silica particles) may be 100:5 to 100:300, or preferably 100:10 to 100:200, or more preferably 100:20 to 100:100. In the case of the same block copolymer in which the inorganic particles are magnetic nanoparticles with an average particle diameter of 5 nm to 1 mm, on the other hand, the content ratio of the inorganic nanoparticles and block copolymer in the of composite (polymer: magnetic nanoparticles on a weight basis) may be 1:10000 or preferably 1:1000 or more preferably 1:100.

Self-assembly of the block copolymer and inorganic particles contained in an aqueous medium can be accomplished conveniently as shown in the conceptual view of a silica-encapsulating RNP preparation method in FIG. 1 by first dissolving the block copolymer (PEG-b-PMNT) in an aqueous medium that has been adjusted to an acidic pH (pH 1 to 5) as necessary, deprotonating by adjusting the pH to weakly acidic to alkaline (pH 6 to 10) as necessary, and agitating. In a different method, self-assembly can be accomplished by first dissolving the block copolymer in a water-soluble organic solvent (such as DMF), adding the inorganic particles, and then dialyzing the resulting mixture with distilled water through a dialysis membrane. Based on the results of dynamic light scattering and the like, it appears that in the composite particles thus formed, the inorganic particles are either encapsulated in the RNP or polymer micelle, or coated with the block copolymer.

The organic-inorganic hybrid composite (or inorganic particle-encapsulating RNP) thus provided can be dispersed uniformly and maintain a stable particle form in bodily fluid. With this RNP, and especially with an RNP in which the inorganic particles are silica and imino (—NH—) groups are included as linking groups in the block copolymer, a stable particle shape is maintained for at least tens of minutes in an acidic, low-pH environment such as gastric fluid. In this Description, the terms bodily fluid, in vivo, physiological and the like are meant to refer to mammals such as humans. When such a silica-encapsulating RNP is manufactured by the second of the aforementioned methods (dialysis method), various drugs and preferably anionic or hydrophobic drugs can be contained or encapsulated in the silica-encapsulating RNP by further including such drugs in the solution before dialysis. Moreover, such drugs can also be added to a solution or dispersion of the previously-prepared silica-encapsulating RNP in an aqueous medium, and agitated and mixed to contain or encapsulate them in the silica-encapsulating RNP. The silica- and drug-containing RNP thus formed maintains a stable particle shape for at least tens of minutes in an acidic environment of low pH such as gastric fluid. An RNP in which the inorganic nanoparticles are magnetic particles and imino (—NH—) groups are included as linking groups in the block copolymer maintains a stable particle shape for a fixed amount of time even in the acidic environment of the body in the same way as the aforementioned silica-encapsulating RNP.

Examples of silica-encapsulating RNPs are explained as specific uses of the composite of the present invention, but these do not limit the applications of the composite of the invention. Silica-encapsulating RNPs (without drugs) contains glucose, sodium, magnesium. calcium, lactic acid and the like that are commonly used in the technical field, and they maintain a stable particle shape even in peritoneal dialysate at low (acidic) pH. Of course, the stable shape of a silica-encapsulating RNP (sometimes called an Si-RNP) can also be maintained in physiologically gentle peritoneal dialysate which the pH is made neutral (6.3 to 7.3) by separating the dialysis pack into two chambers that are mixed immediately before use. Moreover, such silica-encapsulating RNPs improve dialysis efficiency because waste products that pass through the peritoneum and seep outside the body are adsorbed by the silica. Thus, deterioration of the peritoneal membrane, which has been a problem in the past, can be controlled by including silica-encapsulating RNPs in conventional peritoneal dialysate. Considering the presumed mechanism of action of silica-encapsulating RNPs as discussed above, recently proposed peritoneal dialysates (for example, icodextrin-containing peritoneal dialysate containing icodextrin, instead of glucose) are also included as peritoneal dialysates in the sense of the present invention.

As discussed above, a silica- and drug-containing RNP also maintains a stable particle shape for at least tens of minutes in acidic environments of low pH such as gastric fluid. Therefore, this silica- and drug-containing RNP can be used conveniently for efficient delivery of drugs to the intestines via the stomach after oral administration. For example, although this is not a limitation, if the digestive drug rebamipide is selected as the drug, the gastrointestinal sustained release properties of the drug can be obtained because the RNP particle shape is maintained stably for a fixed amount of time in the stomach. As a result, an RNP is provided encapsulating silica together with an anionic drug for delivery to the intestines by oral administration. Such a drug is not limited, but examples include tegafur/uracil, krestin, leucovorin, acetaminophen, cyclophosphamide, melphalan, cytarabine ocfosfate, tegafur-uracil, tegafur/gimestat/otastat potassium combined drug, doxifluridine, hydroxycarbamide, methotrexate, mercaptopurine, etoposide, anastrozole, tamoxifen citrate, toremifene citrate, bicalutamide, flutamide, estramustine phosphate, meloxicam, etodolac, piroxicam, ampiroxixcam, lornoxicam, mofezolac, indometacin farnesil, indometacin, sulindac, fenbufen, diclofenac sodium, nabumetone, loxoprofen sodium, ibuprofen, zaltoprofen, pranoprofen, alminoprofen, naproxen, oxaprozin, tiaprofenic acid, mefenamic acid, tiaramide hydrochloride, azathioprine, tacrolimus, mesalazine, ecabet sodium, rebamipide, aspirin and the like.

Depending on the dosage form, when an RNP encapsulating inorganic particles and any drug is used as an oral preparation, this RNP may exist in self-assembled particle form as discussed above in an aqueous medium for example, or the RNP in any state may be included in a solid preparation, but once the self-assembled particles have been formed in an aqueous medium, they are preferably included in a freeze-dried or other dried form.

Such a medicinal preparation may include diluents, excipients (or carriers) and additives known in the technical field as long as these are consistent with the intent of the present invention, or may be the aforementioned freeze-dried product itself. When the medicinal preparation is a preparation for oral administration in a solid form, the polymerized cyclic nitroxide radical compound can be included together with one or more selected from sucrose, lactose, mannitol, cellulol, trehalose, maltitol, dextran, starch, agar, gelatin, casein, albumin, glyceride and the like. Other inactive diluents, magnesium stearate and other lubricants, paraben, sorbic acid, preservatives such as alpha-tocopherol, antioxidants such as cysteine, disintegrators binders, buffers, sweeteners and the like may also be included.

Liquid preparations for oral administration encompass physiologically acceptable emulsions, syrups, elixirs, suspensions and solution preparations. These preparations may include commonly used inactive diluents such as water. The sugars discussed above and polyethylene glycol with a molecular weight of about 200 to 100,000 may be included in such aqueous solutions.

This preparation may be liquid or semiliquid from the beginning or at the time of use, and in this case it can be made into a parenteral preparation by using physiological saline, buffered physiological saline, sterile water and the like diluents.

BEST MODE FOR CARRYING OUT THE INVENTION

The present invention is explained in detail below, but the intent is not to limit the present invention to these specific embodiments. For purposes of simplification, the explanation is s based on examples using nanoparticles (hereunder sometimes called nRNP) with PEG-b-PCMS-N-TEMPO or PEG-b-PMNT prepared in accordance with Manufacturing Examples 2 and 4 of Patent Document 1 above (the disclosed matter of which becomes the content of this Description by reference) as the polymerized nitroxide radical compound. The values for m and n associated with molecular weights in the examples and the values for nm and μm associated with particle diameter are all average values.

Manufacturing Example 1

Method for Preparing Nitroxide Radical-Containing Nanoparticles Encapsulating Silica (Si-nRNP) (1)

Figure 1:
FIG. 1 is a conceptual diagram showing the preparation of the silica-encapsulating RNP of the invention.

Silica nanoparticles (10 nm, 0.5 mg) were added to an aqueous solution (5 mg/mL, 1 mL, pH 3) of the amphiphatic block polymer PEG-b-PMNT (corresponding to the following formula in which m is about 100 and n is about 20; Mn of m part 4,600, Mn of PCMS converted from 3,300), and agitated at room temperature. Next, sodium hydroxide was added to adjust the pH to 9 and prepare nitroxide radical-containing nanoparticles encapsulating silica (Si-nRNP) (FIG. 1).

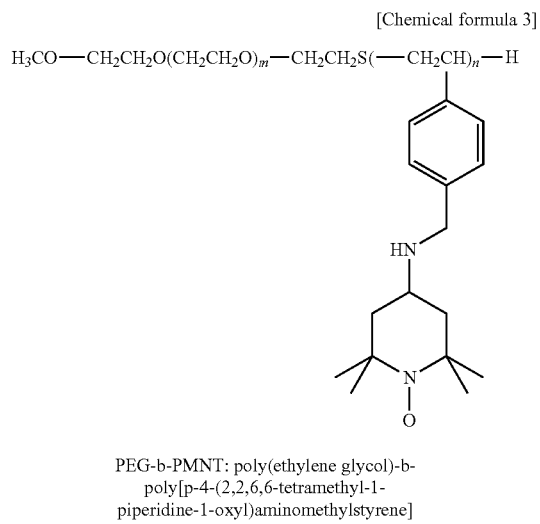

[Chemical formula 3]

$H_3CO$—$CH_2CH_2O(CH_2CH_2O)_m$—$CH_2CH_2S($—$CH_2CH)_n$—$H$

PEG-b-PMNT: poly(ethylene glycol)-b-poly[p-4-(2,2,6,6-tetramethyl-1-piperidine-1-oxyl)aminomethylstyrene]

Figure 2:
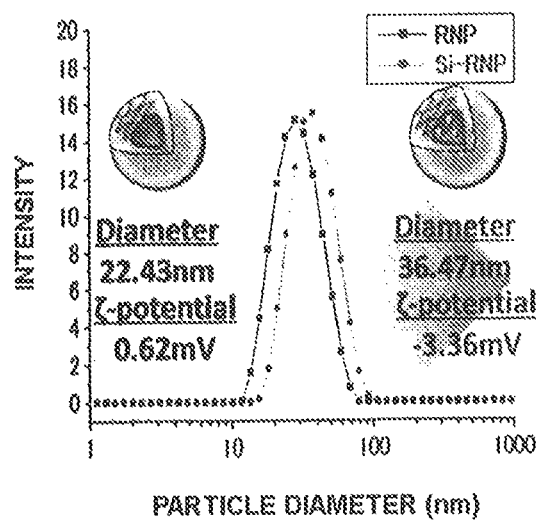
FIG. 2 is a graph showing the results of DLS measurement of nanoparticles obtained in Manufacturing Example 1.

The resulting nanoparticles were shown to have a particle diameter of 37 nm as measured by dynamic light scattering (DLS). Since the particle diameter was 22 nm when no silica nanoparticles were contained (RNP), this suggests that the silica nanoparticles were encapsulated in the Si-RNP (FIG. 2).

Manufacturing Example 2

Method for Preparing Nitroxide Radical-Containing Nanoparticles Encapsulating silica (Si-nRNP) (2)

2 mL of DMF which was passed through a 0.2 μm syringe filter and 10 mg of the amphiphatic block polymer PEG-b-PMNT were added to a vial, and heat was applied with a dryer to completely melt the polymer. A specific amount of silica nanoparticles (Nissan Chemical industries, Ltd., MEK-ST, 10 to 5 nm, 2.1 to 15.5 mg) was further added to the vial. The DMF solution of the polymer was transferred with a Pasteur pipette to a dialysis membrane with a molecular weight cut off of 3,500 that had already been swollen by immersion in water, and dialyzed with 2 L of distilled water.

Dialysis was performed for 24 hours, with the distilled water of the external solution exchanged every few hours. Distilled water was added to the collected solution to a total of 6.5 mL. Sodium chloride was added to this solution at a concentration of 10 mg/ml, after which the solution was passed through a 0.2 μm syringe filter to remove unencapsulated silica particles. Silicon (Si) was assayed with a plasma atomic emission spectrometer to determine the amount of encapsulated silica. The results are shown in Table 1 below.

TABLE 1

| Amount of loaded $SiO_2$ (mg) | $SiO_2$ content (mg) | Particle diameter (nm) | PDI |
|---|---|---|---|
| 2.1 | 0.82 | 80 | 0.21 |
| 5.2 | 2.5 | 85 | 0.29 |
| 10.3 | 6.8 | 92 | 0.22 |
| 15.5 | 10.5 | 82 | 0.28 |

Manufacturing Example 3

Method For Preparing Nitroxide Radical-Containing Nanoparticles Encapsulating Silica (Si-nRNP) (3)

Figure 3:
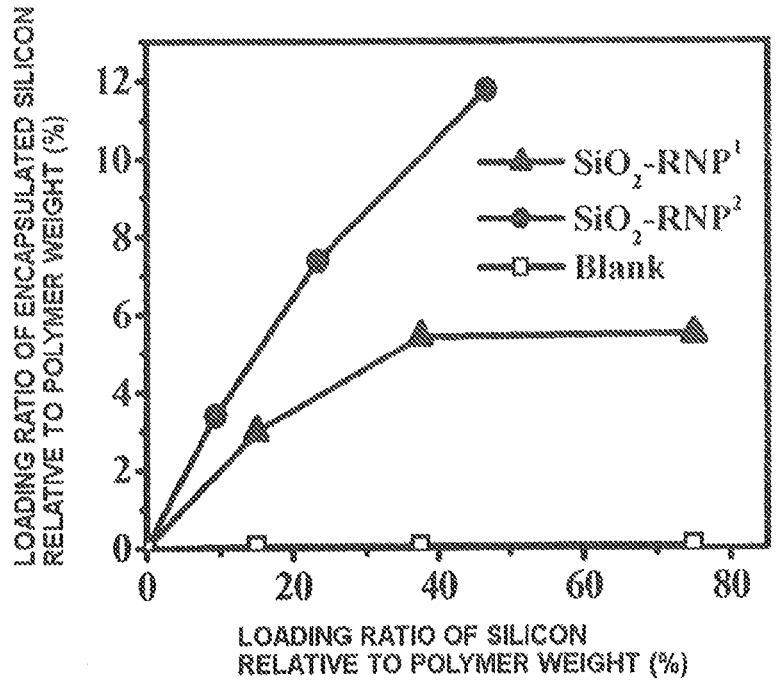
FIG. 3 is a graph showing silica uptake rates relative to the polymer weights of nanoparticles obtained in Manufacturing Example 3, and $SiO_2$-RNP1 indicates results for a particle prepared using TEOS, while $SiO_2$-RNP$^2$ indicates results for a particle prepared using commercial silica particles.

(1) Preparation Method:

A specific amount of tetraethoxysilane (TEOS) or commercial silica particles (Nissan Chemical Industries, Ltd., Snowtex) was added to a 1 mL aqueous solution of nRNP (20 mg/mL), and agitated for 24 hours at 80° C. After agitation this was purified by dialysis with water (MWCO=1,000,000), to obtain nitroxide radical-containing nanoparticles encapsulating silica (Si-nRNP). The amount of encapsulated silica was assayed with a plasma atomic emission spectrometer. The results are shown in FIG. 3.

Figure 4:
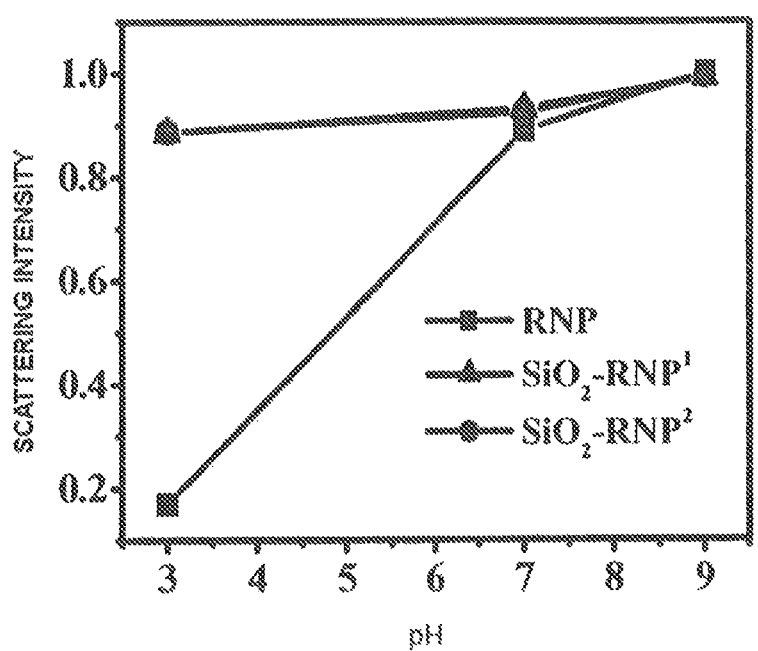
FIG. 4 is a graph showing the stability of the nanoparticles obtained in Manufacturing Example 3 in aqueous solution at various pH values.

(2) Stability of Si-nRNP Obtained above in Aqueous Solution:

Si-nRNP prepared by the methods described above or RNP containing no Si was each incubated for 15 minutes at room temperature in aqueous solutions of the indicated pH values, and the stability of the particles was evaluated according to the light scattering strength. The results are shown in FIG. 4.

Manufacturing Example 4

Encapsulation of the Drug Rebamipide having Anti-inflammatory Properties in Silica-Encapsulating Nanoparticles 1 mL amounts of each of 4 kinds of silica-encapsulating nanoparticles with different silica contents (silica content 0 wt %, 11 wt %, 14 wt %, 36 wt %, 88 wt %/polymer weight) were transferred to microtubes, 3 mg of rebamipide was added to each, and they were agitated for 24 hours at 500 rpm, with an agitator at room temperature. After agitation, they were passed through a 0.2 μm syringe filter to remove the unencapsulated rebamipide.

The silica contents and particle diameters before and after the rebamipide encapsulation operation are shown together in Table 2 below.

TABLE 2

| Silica content before rebamipide encapsulation wt %/polymer weight | Silica content after rebamipide encapsulation wt %/polymer weight | Before rebamipide encapsulation | | After rebamipide encapsulation | |
|---|---|---|---|---|---|
| | | Particle diameter (nm) | PDI | Particle diameter (nm) | PDI |
| 0 | 0 | 63 | 0.27 | 77 | 0.35 |
| 12 | 8.5 | 81 | 0.21 | 110 | 0.25 |
| 14 | 11 | 72 | 0.23 | 135 | 0.33 |
| 36 | 31 | 75 | 0.24 | 174 | 0.26 |
| 88 | 40 | 66 | 0.19 | 184 | 0.28 |

In the table, PDI represents the polydispersity index.

Test Example 1

Analysis of Rebamipide Contents of Prepared Rebamipide-Encapsulating particles

The rebamipide contents of the prepared rebamipide-encapsulating particles were analyzed by measuring the absorption spectrum at 330 nm, which is the absorption maximum wavelength of rebamipide. The results are shown in FIG. 5.

Figure 5:
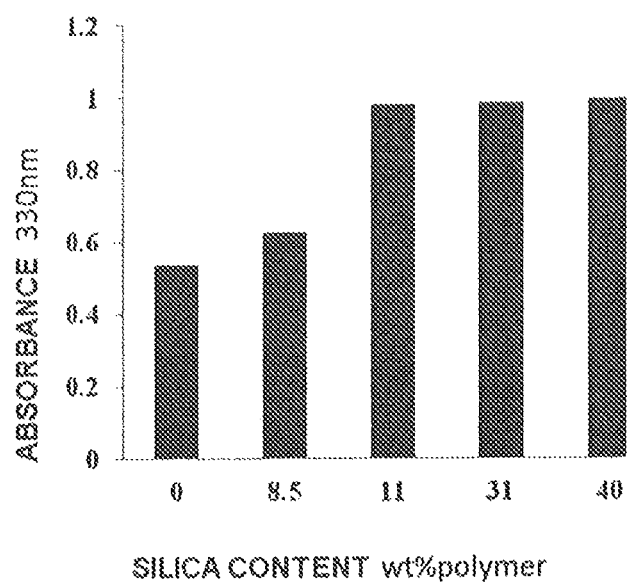
FIG. 5 is a graph showing the results of analysis in Test 1 of the rebamipide contents of rebamipide-encapsulating particles prepared in Manufacturing Example 4.

It can be seen from FIG. 5 that more rebamipide is encapsulated in the nanoparticles containing silica than in the nanoparticles containing no silica, Test Example 2

Stability of Drug-Encapsulating Nanoparticles under Acidic Conditions

Changes in scattering intensity at pH 3 were measured in order to evaluate the stability of nanoparticles (containing 8.5 wt silica per polymer weight) encapsulating the rebamipide of Manufacturing Example 4 as a drug under acidic conditions. 350 μL of deionized water and 40 μL of buffer (pH 3) were added to a disposable low size cuvette and agitated by pipetting, after which 10 μL of the sample was added and scattering intensity was measured. The conditions for measurement were set at 1 measurement per minute, with measurement beginning 4 minutes after the pH was adjusted to 3, and scattering intensity measured continuously for 15 minutes. The results are shown in FIG. 6.

Figure 6:
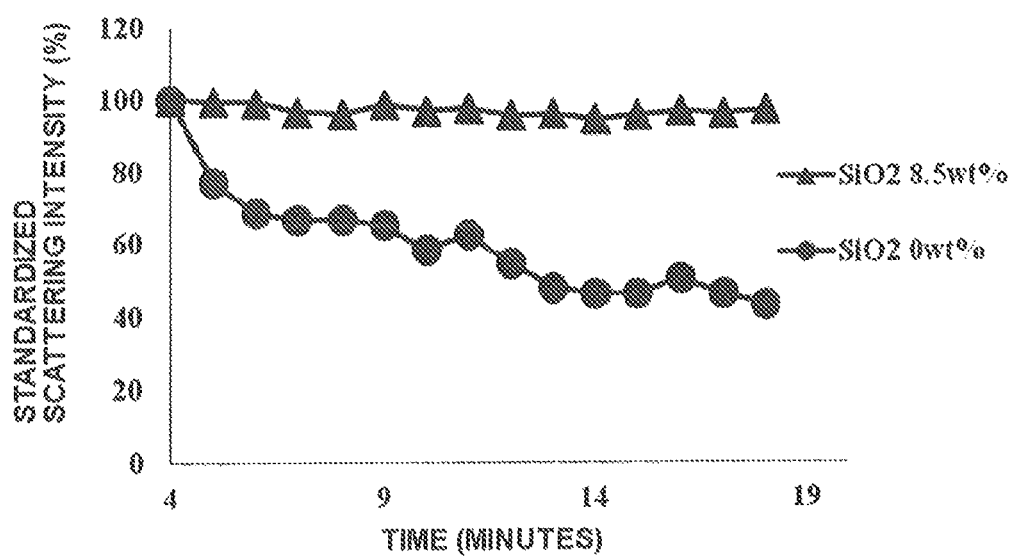
FIG. 6 is a graph showing results for stability of drug-containing nanoparticles under acidic conditions as analyzed by dynamic light scattering (DLS) in Test Example 2, and the curve with the black triangles represents a silica content ratio of 8.5% per polymer weight, while the curve with black circles represents a silica content ratio of 0 wt % per polymer weight.

In FIG. 6, scattering intensity fell to about 40%, which is the initial scattering intensity, after 20 minutes in the case of the nanoparticles containing no silica, while almost no change in scattering intensity was observed with the silica-encapsulating nanoparticles. This confirms that the nanoparticles remain stable even in an acidic environment.

Test Example 3

Release Behavior of Encapsulated Drug in Nanoparticles Left under Acidic Conditions Nanoparticles (the same as those of Test Example 2 above) were left for 20 minutes under acidic conditions of pH 3, and the release behavior of the encapsulated drug rebamipide was evaluated. If the rebamipide is released when the nanoparticles break down under acidic conditions, it can be removed by passage through a 0.2 μm syringe filter.

Figure 7:
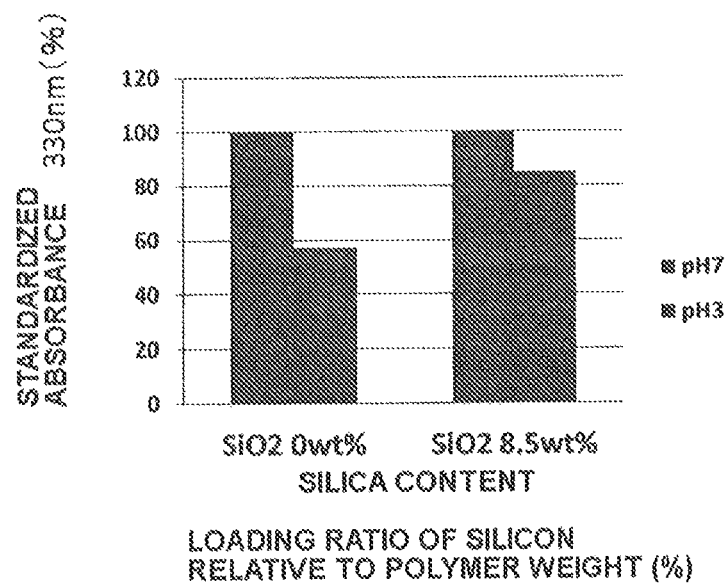
FIG. 7 is a graph showing the release behavior of an encapsulated drug when nanoparticles were left in an acidic environment in Test Example 3.

The encapsulated rebamipide content of the nanoparticles left under acidic conditions was measured using absorption measured under conditions of pH 7 as the standard for encapsulated rebamipide content (100%), and the percentage of released rebamipide was calculated. The results are shown in FIG. 7.

While 43% of the encapsulated drug was released from the nanoparticles without silica, release was reduced to 17% by the inclusion of 8.5 wt % silica (as a percentage of polymer weight).

These results confirm that a drug can be encapsulated more stably under acidic conditions with nanoparticles containing silica, than with nanoparticles containing no silica.

Test Example 4

Test of Urea Adsorption Ability of Silica-Encapsulating Nanoparticles

Figure 8:
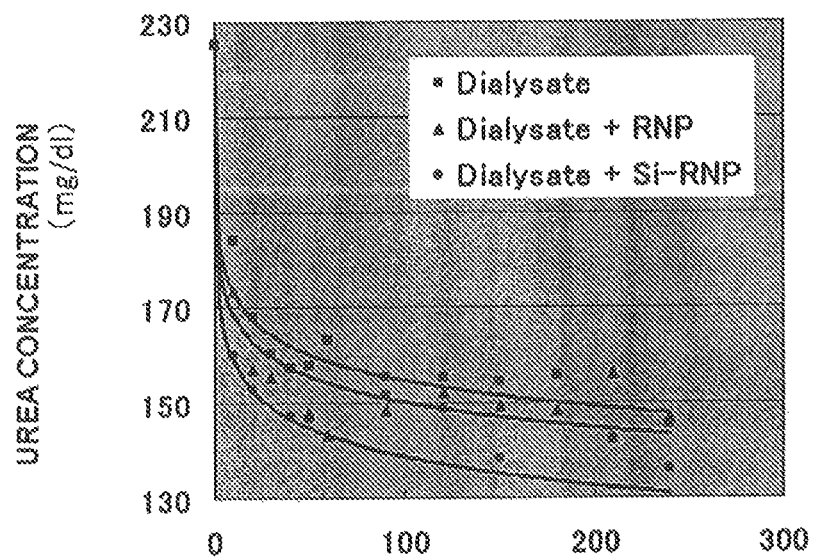
FIG. 8 is a graph showing the efficiency of urea adsorption by silica-encapsulating nanoparticles in Test Example 4.

As a peritoneal dialysis model, a dialysis membrane (molecular weight cutoff 12,000 to 14,000) containing a dialysate (Dianeal NPD-4, Baxter, ingredients (w/v%) glucose 1.36, calcium chloride 0.0183, magnesium chloride 0.00508, sodium lactate 0.448, sodium chloride 0.538, volume 10 mL) and Si-nRNP (polymer concentration 5 mg/mL, silica gel concentration 0.25 mg/mL) was immersed in a urea solution (190 mg/dL, 20 mL), and the amount of urea in the external solution was assayed by colorimetric assay. The results for amount of urea in the external solution are shown in FIG. 8. The dialysis rates were similar using the RNP-containing dialysate and a commercially used dialysate, but dialysis efficiency was obviously greater using Si-nRNP. This result shows that dialysis time and efficiency are improved by using Si-nRNP as a dialysate.

Test Example 5

Figure 9:
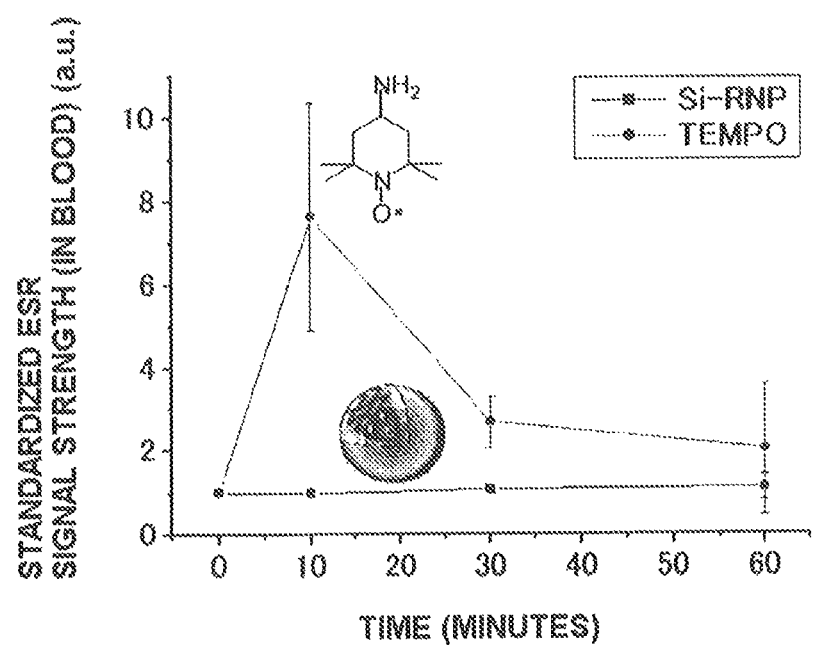
FIG. 9 is a graph showing the results of a blood uptake suppression test after intraperitoneal administration of Si-RNP in Test Example 5.

Test of Blood Uptake Suppression after Intraperitoneal Administration of Si-nRNP Normally, low-molecular-weight compounds are taken up into the blood after intraperitoneal administration, and are at risk of dispersing throughout the body. FIG. 9 shows the results when the low-molecular-weight compound TEMPO was actually administered intraperitoneally, and the electron spin resonance (ESR) signal was then measured in blood. It is clear from FIG. 9 that the drug is present in blood for an hour or more. High-dosage administration of low-molecular-weight TEMPO causes side-effects including reduced blood pressure and inhibition of the mitochondrial energy-transfer system. On the other hand, it has been confirmed that a silica-encapsulating RNP (Si-nRNP) has no blood mobility because it does not pass at all through the peritoneal membrane. These data indicate that this could be an extremely safe, promising dialysate, with no need for concern about systemic toxicity.

Test Example 6

Therapeutic Results Using Si-nRNP with Peritoneal Sclerosis Model Animal

Figure 10:
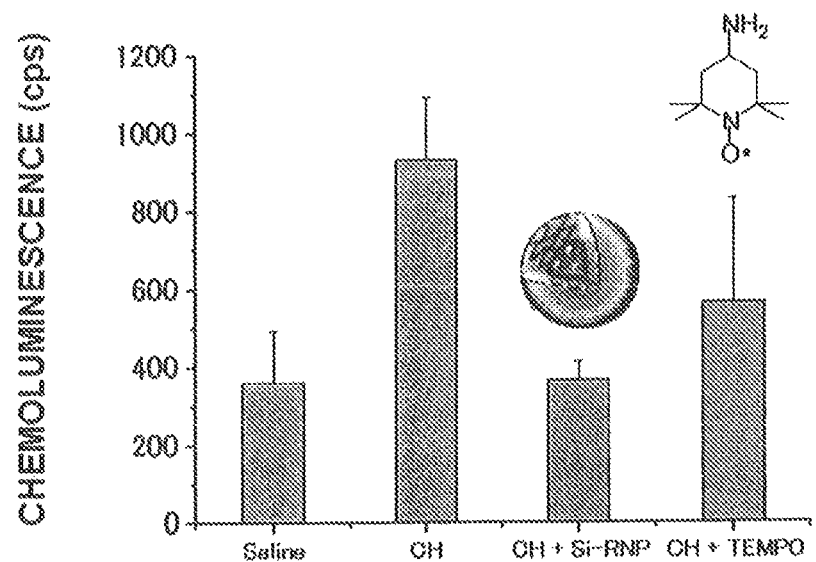
FIG. 10 is a graph showing therapeutic results with RNP using a peritoneal sclerosis model animal in Test Example 6.

Peritoneal sclerosis model rats were prepared by administering 0.1% (v/v) chlorhexidine gluconate intraperitoneally every day for a Week. Saline, Si-nRNP, or the low-molecular-weight compound TEMPOL was also administered every day for a week at the same time, and the peritoneal deterioration suppressing effects were investigated by assaying the amount of superoxides produced by peritoneal inflammation. The results are shown in FIG. 10.

When the rats were dissected after 1 week and the peritoneal membranes were homogenized and evaluated with a superoxide-reactive chemiluminescent reagent (MPEC: 2-methyl-6-p-methoxyphenylethynyl imidazopyrazinone), it was shown that Si-RNP suppresses superoxide production caused by chlorhexidine gluconate, and is much more effective than the low-molecular-weight compound TEMPOL.

Manufacturing Example 5

Method of Preparing Nitroxide Radical-Containing nanoparticle Encapsulating Magnetic Particles (Fe-nRNP): Surface Modification at pH 7.4 (Physiological Conditions)

PEG-b-PMNT in which the degree of polymerization of the cationic PMNT segment was 5, 10, 20 and 30 units (unit: corresponds to the value n in the formula of Manufacturing Example 1), respectively, was weighed onto 1.5 mL microtubes in amounts of 50, 100 and 200 molar amino equivalents each relative to the carboxyl groups of the magnetic particles (90 µg, carboxyl groups 22.5 nmol, obtained from Life Technologies Corporation, product name Dynabeads (r) M-270 Carboxylic Acid, particle diameter 2.8 µm). The quantities are shown in Table 3. 10 µL of 0.1 M HCl was added to the PEG-b-PMNT to dissolve the PEG-b-PMNT, 3 µL of magnetic particles (90 µg, 22.5 carboxyl moles) and 240 mL of pH 7.4 phosphate buffer were added, and the pH was measured. The pH was adjusted to 7.4 with 0.1 M NaOH and 0.1 M HCl, and the mixture was agitated for about 24 hours. After agitation, the PEG-b-PMNT modified magnetic particles (Fe-nRNP) were accumulated on the wall surface with a magnet to exclude non-adsorbed PEG-b-PMNT that had not been adsorbed by the magnetic particle surfaces, and the solution was washed. After addition of 250 µL of pH 7.4 phosphate buffer, this was agitated, and non-adsorbed PEG-b-PMNT was removed by removing the solution in the same way. This operation was repeated 4 times to completely remove the non-adsorbed PEG-b-PMNT. To confirm removal, washing liquid was collected from the 4th washing, and measured by electron spin resonance (ESR) to confirm the elimination of the signal. The amount of PEG-b-PMNT modification was determined by ESR measurement from the integral value of the electron spin spectrum.

TABLE 3

| Number of units | Unit equivalents | | |
| --- | --- | --- | --- |
| | 50eq | 100eq | 200eq |
| 5 unit | 1.5 [mg] | 3.0 [mg] | |
| 10 unit | 1.0 [mg] | 2.0 [mg] | 4.0 [mg] |
| 20 unit | 0.6 [mg] | 1.2 [mg] | 2.4 [mg] |
| 30 unit | 0.5 [mg] | 1.0 [mg] | 2.0 [mg] |

Figure 11:
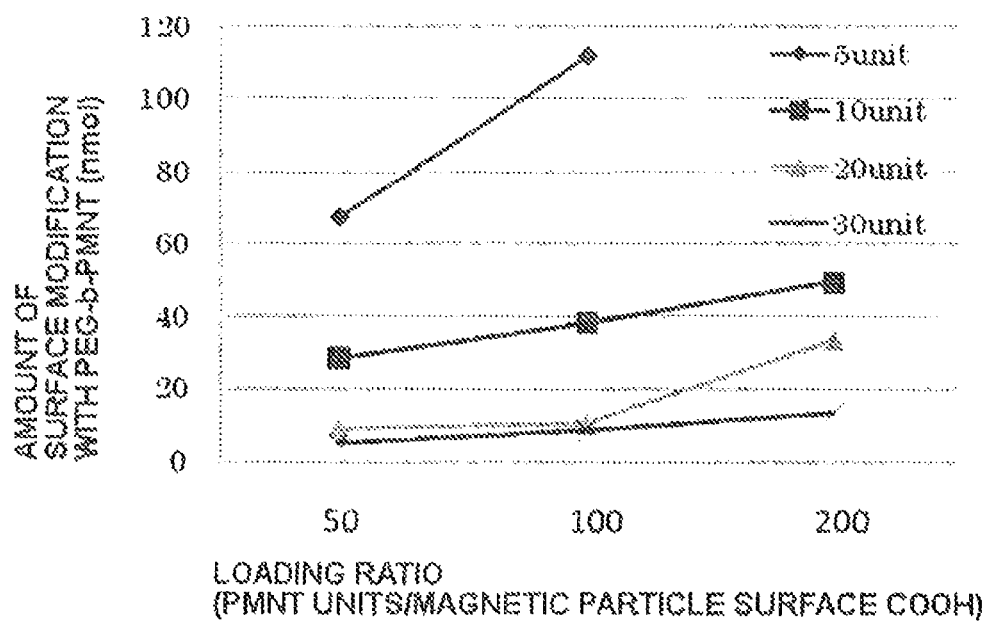
FIG. 11 is a graph showing amounts of PEG-b-PMNT with modified magnetic particles obtained in Manufacturing Example 5.

The results for amount of surface modification with PEG-b-PMNT are shown together in FIG. 11. It can be seen from FIG. 11 that as in the results above, the amount of modification is greater when the chain length is shorter. It is also shown that the amount of the magnetic particles modified with PEG-b-PMNT increases dependently on the added amount of PEG-b-PMNT.

INDUSTRIAL APPLICABILITY

The organic-inorganic hybrid compound of the present invention can itself improve the properties of a peritoneal dialysate for example, and when it also contains another drug, can serve as a carrier for delivery of that drug to the intestines by oral administration. Thus, it can be used in the pharmaceutical field for example.

The invention claimed is:

1. An organic-inorganic hybrid composite comprising inorganic particles and a polymer,
   wherein the inorganic particles are selected from the group consisting of silica particles and magnetic particles, and
   the polymer is a block copolymer represented by Formula (I):

PEG-CNR     (I)

in which PEG is a segment containing poly(ethylene glycol), and
   CNR is a polymer segment having a repeating unit containing, as part of a pendant group, a cyclic nitroxide radical that binds to a polymer main chain via a linking group,
   and wherein the hybrid composite is, when dissolved or dispersed in water, in the form of a polymer micelle having an average particle diameter of 5 nm to 500 nm.

2. The composite according to claim 1, wherein the hybrid composite in the form of a polymer micelle comprises silica particles.

3. The composite according to claim 1, wherein the hybrid composite in the form of a polymer micelle comprises one or more magnetic particles selected from the group consisting of $Fe_3O_4$, $\gamma$-$Fe_2O_3$ and FePt.

4. The composite according to Claim 1, wherein the linking group of the block copolymer contains at least one imino (—NH—) or oxy (—O—).

5. The composite according to claim 1, wherein the linking group of the block copolymer is o- or p-phenylene-$C_{1-6}$ alkylene-NH-$(C_{1-6}$ alkylene$)_q$- or o- or p-phenylene-$C_{1-6}$ alkylene—O—$(C_{1-6}$ alkylene$)_q$, in which q is 0 or 1, the cyclic nitroxide radical that binds to the polymer main chain via this linking group is selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl,
   and the polymer main chain is derived from polymerizable unsaturated double bonds, and unbound termini of the phenylenes bind to this main chain.

6. An organic-inorganic hybrid composite comprising inorganic particles and a polymer,
   wherein the hybrid composite is, when dissolved or dispersed in water, in the form of a polymer micelle having an average particle diameter of 5 nm to 500 nmand
   the polymer is represented by General Formula (II):

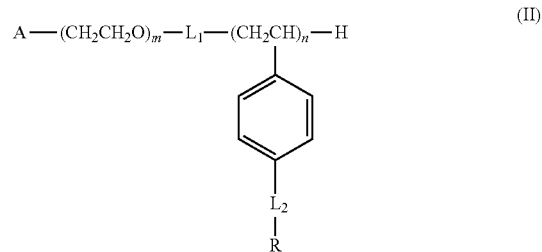

$$A-(CH_2CH_2O)_m-L_1-(CH_2CH)_n-H \quad (II)$$

in which A represents an unsubstituted or substituted $C_1$-$C_{12}$ alkoxy, with the substituent if any being a formyl group or a group represented by R¹R² CH-, in which R¹ and R² are independently $C_1$-$C_4$ alkoxy groups or R¹ and R² together form —OCH₂CH₂O—, —O(CH₂)₃O— or —O(CH₂)₄O—;

$L_1$ is selected from the group consisting of a single bond, -(CH₂)$_c$S— and —CO(CH₂)$_c$S—, in which c is an integer from 1 to 5;

$L_2$ is —$C_{1-6}$ alkylene-NH—($C_{1-6}$ alkylene)$_q$- or —$C_{1-6}$ alkylene-O-($C_{1-6}$ alkylene)$_q$-, in which q is 0 or 1;

R is selected from the group consisting of 2,2,6,6-tetramethylpiperidine-1-oxyl-4-yl, 2,2,5,5-tetramethylpyrrolidine-1-oxyl-3-yl, 2,2,5,5-tetramethylpyrroline-1-oxyl-3-yl, 2,4,4-trimethyl-1,3-oxazolidine-3-oxyl-2-yl, 2,4,4-trimethyl-1,3-thiazolidine-3-oxyl-2-yl and 2,4,4-trimethyl-imidazolidine-3-oxyl-2-yl;

$L_2$-R is present in at least 50% of the total number n, and when it is not present, the remaining $L_2$-R parts may be methyl, halomethyl or hydroxymethyl groups;

m is an integer from 20 to 5,000; and n is independently an integer from 3 to 1,000.

7. The composite according to claim 6, wherein R is selected from the groups represented by the following formulae:

[Chemical formula 2]

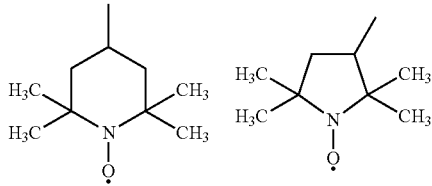

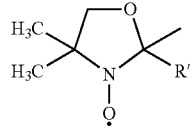

in which R' is a methyl group, and $L_2$-R is present in at least 80% of the total number n.

8. The composite according to claim 6, wherein $L_2$ is —$C_{1-6}$ alkylene-NH—($C_{1-6}$ alkylene)$_q$-.

9. The composite according to claim 6, wherein $L_2$ is -$C_{1-6}$ alkylene-O—($C_{1-6}$ alkylene)$_q$-.

10. The composite according to claim 6, wherein the inorganic particles are silica particles.

11. The composite according to claim 6, wherein the inorganic particles are magnetic particles.

12. A medicinal composition comprising: the composite according to claim 6 in which the inorganic particles are silica particles; and a pharmaceutically acceptable diluent or excipient.

13. A medicinal composition comprising: the composite according to claim 6 in which the inorganic particles are silica particles; and a pharmaceutically acceptable diluent or excipient, the medicinal composition being in the form of a peritoneal dialysate.

14. A medicinal composition comprising: the composite according to claim 6 in which the inorganic particles are silica particles; and a drug to be delivered to the intestines by oral administration.

15. A peritoneal dialysate comprising the organic-inorganic hybrid composite of claim 6 as an active ingredient.

* * * * *